(12) United States Patent
Kölling

(10) Patent No.: US 7,795,441 B2
(45) Date of Patent: Sep. 14, 2010

(54) PROCESS FOR PREPARING IMINO COMPOUNDS

(75) Inventor: Lars Kölling, Mannheim (DE)

(73) Assignee: Basell Polyolefine GmbH, Wesseling (DE)

( * ) Notice: Subject to any disclaimer, the term of this patent is extended or adjusted under 35 U.S.C. 154(b) by 3 days.

(21) Appl. No.: 12/087,533

(22) PCT Filed: Jan. 12, 2007

(86) PCT No.: PCT/EP2007/000255

§ 371 (c)(1),
(2), (4) Date: Jul. 9, 2008

(87) PCT Pub. No.: WO2007/080121

PCT Pub. Date: Jul. 19, 2007

(65) Prior Publication Data

US 2009/0005571 A1    Jan. 1, 2009

Related U.S. Application Data

(60) Provisional application No. 60/798,866, filed on May 9, 2006.

(30) Foreign Application Priority Data

Jan. 13, 2006   (DE)   ...................... 10 2006 001 960

(51) Int. Cl.
*C07D 211/70* (2006.01)
(52) U.S. Cl. ....................................................... 546/328
(58) Field of Classification Search ................ 546/329, 546/328
See application file for complete search history.

(56) References Cited

U.S. PATENT DOCUMENTS

| 4,442,095 | A | 4/1984 | Johnston |
| 4,479,953 | A | 10/1984 | Friedman |
| 4,507,299 | A | 3/1985 | Johnston |
| 5,955,555 | A | 9/1999 | Bennett |
| 6,710,006 | B2 | 3/2004 | De Boer et al. |
| 2004/0092521 | A1 | 5/2004 | Altenbach et al. |

FOREIGN PATENT DOCUMENTS

WO    WO 0234746    *   5/2002

OTHER PUBLICATIONS

Burstein et. al., "Imidazo[1,5-a]pyridine-3-ylidenes-pyridine derived N-heterocyclic carbene ligands", Tetrahedron 61 (2005), pp. 6207-6217.*
Bianchini et. al., "Oligomerisatin of ethylene to linear alpha-olefins by tetrahedral cobalt (II) precursors stabilised by benzo[b]thiophen-2-yl-substituted (imino) pyridine ligands", Journal of Organometallic Chemistry 689 (2004), pp. 1356-1361.*
Parks et al., "Syntheses Employing Pyridyllithium Reagents: New Routes To 2,6-Disubstituted Pyridines And 6,6'Disubstituted 2,2' Bipyridyls", *J. Organomet. Chem. 546* 1973, pp. 53-66.
Furukawa et al., "Preparation Of Pyridyl Grignard Reagents And Cross Coupling Reactions With Sulfoxides Bearing Azaheterocycles", *Tetrahedron Lett.*, 28 5845 (1987).
Brandsma, et al., *Preparative Polar Organometallic Chemistry*, vol. 1, pp. 30-31 and pp. 142-143, Springer-Verlag 1987.
Bianchini et al., "Oligomerisation Of Ethylene To Linear A-Olefins By Tetrahedral Cobalt(II) Precursors Stabilised By Benzo[*B*]Thiophen-2-Yl-Substituted (Imino) Pyridine Ligands", *Journal of Organometallic Chemistry*, 689 (2004) 1356-1361.
Small et al., "New Chromium Complexes Of Tridentate Ligands In Metal-Catalyzed Olefin Polymerization", *Macromolecules* 2004, 37, 4375-4386.
Burstein et al., "Imidazo[1,5-*A*]Pyridine-3-Ylidenes—Pyridine Derived N-Heterocyclic Carbine Ligands", *Tetrahedron 61* (2005) 6207-6217.
Database Beilstein, Beilstein Institute for Organic Chemistry, Frankfurt—Main, DE; Citation No. 6195728 1996, XP002434857, Reaction IDs 5250757 5250756 abstract.
Database Beilstein, Beilstein Institute for Organic Chemistry, Frankfurt—Main, DE; Reaction ID 1805846 1981, XP002434857 abstract.
Lee et al., "Synthesis And Biological Activity Of Anthelmintic Thiadiazoles Using An AF-2 Receptor Binding Assay", *Bioorganic & Medicinal Chemistry Letters 9* (1999) 1727-1732.
Database Beilstein, Beilstein Institute for Organic Chemistry, Frankfurt—Main, DE; Citation No. 1022124 BRN 182850 1932, XP002434858 abstract.
Database Beilstein, Beilstein Institute for Organic Chemistry, Frankfurt—Main, DE; Citation No. 1075615 BRN 206699 1933, XP002434859 abstract.

* cited by examiner

*Primary Examiner*—Janet L Andres
*Assistant Examiner*—Binta M Robinson
(74) *Attorney, Agent, or Firm*—Jonathan L. Schuchardt

(57) ABSTRACT

Process for preparing imine compounds, in which a carbonyl compound is reacted with a primary amine. The imine compound obtained in this way can be reacted further with a metalalkyl and subsequently a carbonyl compound to form an imine compound.

7 Claims, No Drawings

PROCESS FOR PREPARING IMINO COMPOUNDS

CROSS-REFERENCE TO RELATED APPLICATIONS

This application is a national phase filing under 35 U.S.C. §371 of International Application PCT/EP2007/000255, filed 12 Jan. 2007, claiming priority to German Patent Application 10 2006 001 960.1 filed 13 Jan. 2006 and provisional U.S. Appl. No. 60/798,866 filed 9 May 2006; the disclosures of International Application PCT/EP2007/000255, German Pat. Appl. 10 2006 001 960.1, and U.S. Appl. No. 60/798,866, each as filed, are incorporated herein by reference.

The present invention relates to a process for preparing imino compounds.

The use of metallocene catalysts in the polymerization of unsaturated compounds has a great influence on the preparation of polyolefins since it opens up a route to new types of polyolefinic materials or to materials having improved properties. There is therefore great interest in the development of novel families of catalysts for the polymerization of unsaturated compounds in order to obtain even better control over the properties of polyolefins and further novel products.

The use of transition metal catalysts comprising late transition metals is of particular interest due to their ability to tolerate heteroatom functions. Transition metal catalysts derived from late transition metals which are suitable for the polymerization of unsaturated compounds are known from the prior art. Among these, 1,2-diiminenickel and 2,6-bis(imino)pyridyliron complexes have been found to be particularly useful.

The preparation of unsymmetrical 2,6-bis(imino)pyridyl compounds which bear two different imino groups is usually carried out via a first condensation of the corresponding diketo compounds with a primary amine. The intermediate obtained is then reacted with a second primary amine which is different from the first. In the first step, not only the monoimine but also the symmetrical diimine product are formed, so that the yield of the intermediate is usually very low. Particularly when primary amines having electron-pulling or relatively nonbulky groups are used, the yield of monoimine intermediate drops.

WO 98/27124 discloses the synthesis of unsymmetrical 2,6-bis(imino)pyridyl compounds from the corresponding diketo compounds and anilines in toluene with addition of catalytic amounts of toluenesulfonic acid via monoimine intermediates. Monoimine intermediates having electron-pulling substituents are not disclosed.

When anilines which bear an electron-pulling substituent in the ortho position are used, the yield of monoimine intermediate is very low. It is an object of the present invention to provide an improved process for the synthesis of the monoimine intermediate, by means of which even primary amines having electron-pulling or relatively nonbulky substituents can be converted into the corresponding monoimine compounds in improved yields. These monoimine compounds are particularly well-suited as starting materials for the synthesis of unsymmetrical diimine compounds and lead to higher yields of unsymmetrical product.

We have accordingly found a process for preparing imine compounds of the formula I,

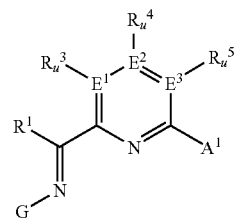

where the variables have the following meanings:

$A^1$ is chlorine, bromine or iodine, the radicals $R^1$ are each, independently of one another, hydrogen, $C_1$-$C_{22}$-alkyl, $C_2$-$C_{22}$-alkenyl, $C_6$-$C_{22}$-aryl, arylalkyl having from 1 to 10 carbon atoms in the alkyl radical and 6-20 carbon atoms in the aryl radical or a five-, six- or seven-membered heterocycle comprising at least one atom from the group consisting of N, P, O and S, where the organic radical $R^1$ may also be substituted by halogens, $NR^{11}{}_2$, $OR^{11}$ or $SiR^{12}{}_3$ and/or the radical $R^1$ may also be joined to $R^3$ to form a five-, six- or seven-membered ring, $R^3$-$R^5$ are each, independently of one another, hydrogen, $C_1$-$C_{22}$-alkyl, $C_2$-$C_{22}$-alkenyl, $C_6$-$C_{22}$-aryl, arylalkyl having from 1 to 10 carbon atoms in the alkyl radical and 6-20 carbon atoms in the aryl radical, $NR^{11}{}_2$, $OR^{11}$, halogen, $SiR^{12}{}_3$ or a five-, six- or seven-membered heterocycle comprising at least one atom from the group consisting of N, P, O and S, where the organic radicals $R^3$-$R^5$ may also be substituted by halogens, $NR^{11}{}_2$, $OR^{11}$ or $SiR^{12}{}_3$ and/or two radicals $R^3$-$R^5$ may also be joined to one another to form a five-, six- or seven-membered ring and/or two radicals $R^3$-$R^5$ may be joined to one another to one another to form a five-, six- or seven-membered heterocycle comprising at least one atom from the group consisting of N, P, O and S, the radicals $R^{11}$ are each, independently of one another, hydrogen, $C_1$-$C_{22}$-alkyl, $C_2$-$C_{22}$-alkenyl, $C_6$-$C_{22}$-aryl, arylalkyl having from 1 to 10 carbon atoms in the alkyl radical and 6-20 carbon atoms in the aryl radical or $SiR^{12}{}_3$, where the organic radicals $R^{11}$ may also be substituted by halogens and two radicals $R^{11}$ may also be joined to form a five- or six-membered ring and the radicals $R^{12}$ are each, independently of one another, hydrogen, $C_1$-$C_{22}$-alkyl, $C_2$-$C_{22}$-alkenyl, $C_6$-$C_{22}$-aryl or arylalkyl having from 1 to 10 carbon atoms in the alkyl radical and 6-20 carbon atoms in the aryl radical and two radicals $R^{12}$ may also be joined to form a five- or six-membered ring, G is $C_1$-$C_{22}$-alkyl, $C_2$-$C_{22}$-alkenyl, $C_6$-$C_{40}$-aryl, arylalkyl having from 1 to 10 carbon atoms in the alkyl radical and 6-20 carbon atoms in the aryl radical, $NR^{11}{}_2$, $SiR^{12}{}_3$ or a five-, six- or seven-membered heterocycle comprising at least one atom from the group consisting of N, P, O and S, where the organic radical G may also be substituted by halogens, $NR^{11}{}_2$, $OR^{11}$ or $SiR^{12}{}_3$, $E^1$-$E^3$ are each, independently of one another, carbon, nitrogen or phosphorus, in particular carbon, and u is 0 when $E^1$-$E^{13}$ is nitrogen or phosphorus and is 1 when $E^1$-$E^3$ is carbon, which comprises the following steps:

A) reaction of a carbonyl compound of the formula II

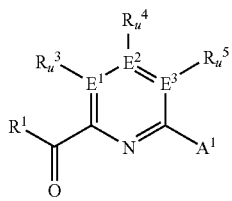

with a primary amine G-NH$_2$, where the variables are as defined above.

Furthermore, we have found imine compounds of the formula I.

In the process of the invention, a primary amine is any compound which bears an NH$_2$ group, i.e. including hydrazines.

As primary amine, use is made of G-NH$_2$, where the meaning of G and its preferred embodiments is the same as for the imine compound of the formula I. Examples of primary amines are methylamine, ethylamine, n-propylamine, isopropylamine, n-butylamine, tert-butylamine, sec-butylamine, isobutylamine, tert-amylamine, n-pentylamine, n-hexylamine, n-octylamine, cyclohexylamine, aniline, 2-methylaniline, 2-chloroaniline, 2-bromoaniline, 2,6-dichloroaniline, 2,4-dichloro-6-methylaniline and 2,6-dibromoaniline. G preferably comprises a halogen-comprising substituent.

Preference is given to imine compounds of the formula Ia,

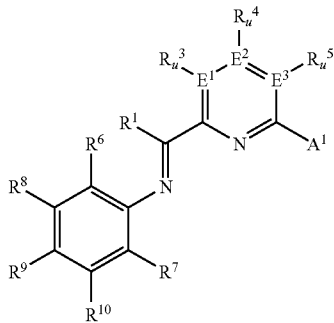

where the variables have the following meanings:

A$^1$ is chlorine, bromine or iodine, the radicals R$^1$ are each, independently of one another, hydrogen, C$_1$-C$_{22}$-alkyl, C$_2$-C$_{22}$-alkenyl, C$_6$-C$_{22}$-aryl, arylalkyl having from 1 to 10 carbon atoms in the alkyl radical and 6-20 carbon atoms in the aryl radical or a five-, six- or seven-membered heterocycle comprising at least one atom from the group consisting of N, P, O and S, where the organic radical R$^1$ may also be substituted by halogens, NR$^{11}_2$, OR$^{11}$ or SiR$^{12}_3$ and/or the radical R$^1$ may also be joined to R$^3$ to form a five-, six- or seven-membered ring, R$^3$-R$^{10}$ are each, independently of one another, hydrogen, C$_1$-C$_{22}$-alkyl, C$_2$-C$_{22}$-alkenyl, C$_6$-C$_{22}$-aryl, arylalkyl having from 1 to 10 carbon atoms in the alkyl radical and 6-20 carbon atoms in the aryl radical, NR$^{11}_2$, OR$^{11}$, halogen, SiR$^{12}_3$ or a five-, six- or seven-membered heterocycle comprising at least one atom from the group consisting of N, P, O and S, where the organic radicals R$^3$-R$^{10}$ may also be substituted by halogens, NR$^{11}_2$, OR$^{11}$ or SiR$^{12}_3$ and/or two radicals R$^3$-R$^5$ or two radicals R$^6$-R$^{10}$ may also be joined to one another to form a five-, six- or seven-membered ring and/or two radicals R$^3$-R$^5$ or two radicals R$^6$-R$^{10}$ may be joined to one another to form a five-, six- or seven-membered heterocycle comprising at least one atom from the group consisting of N, P, O and S, the radicals R$^{11}$ are each, independently of one another, hydrogen, C$_1$-C$_{22}$-alkyl, C$_2$-C$_{22}$-alkenyl, C$_6$-C$_{22}$-aryl, arylalkyl having from 1 to 10 carbon atoms in the alkyl radical and 6-20 carbon atoms in the aryl radical or SiR$^{12}_3$, where the organic radicals R$^{11}$ may also be substituted by halogens and two radicals R$^{11}$ may also be joined to form a five- or six-membered ring and the radicals R$^{12}$ are each, independently of one another, hydrogen, C$_1$-C$_{22}$-alkyl, C$_2$-C$_{22}$-alkenyl, C$_6$-C$_{22}$-aryl or arylalkyl having from 1 to 10 carbon atoms in the alkyl radical and 6-20 carbon atoms in the aryl radical and two radicals R$^{12}$ may also be joined to form a five- or six-membered ring, E$^1$-E$^3$ are each, independently of one another, carbon, nitrogen or phosphorus, in particular carbon, and u is 0 when E$^1$-E$^3$ is nitrogen or phosphorus and is 1 when E$^1$-E$^3$ is carbon.

Here, primary amines G-NH$_2$ used are anilines of the formula III

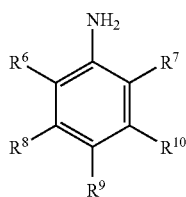

where the variables are as defined above.

G is preferably

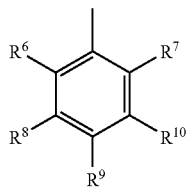

where the variables have the following meanings:

R$^6$-R$^{10}$ are each, independently of one another, hydrogen, C$_1$-C$_{22}$-alkyl, C$_2$-C$_{22}$-alkenyl, C$_6$-C$_{22}$-aryl, arylalkyl having from 1 to 10 carbon atoms in the alkyl radical and 6-20 carbon atoms in the aryl radical, NR$^{11}_2$, OR$^{11}$, halogen, SiR$^{12}_3$ or a five-, six- or seven-membered heterocycle comprising at least one atom from the group consisting of N, P, O and S, where the organic radicals R$^6$-R$^{10}$ may also be substituted by halogens, NR$^{11}_2$, OR$^{11}$ or SiR$^{12}_3$ and/or two radicals R$^6$-R$^{10}$ may also be joined to one another to form a five-, six- or seven-membered ring and/or two radicals R$^6$-R$^{10}$ are joined to one another to form a five-, six- or seven-membered heterocycle comprising at least one atom from the group consisting of N, P, O and S, the radicals R$^{11}$ are each, independently of one another, hydrogen, C$_1$-C$_{22}$-alkyl, C$_2$-C$_{22}$-alkenyl, C$_6$-C$_{22}$-aryl, arylalkyl having from 1 to 10 carbon atoms in the alkyl radical and 6-20 carbon atoms in the aryl radical or $SiR^{12}_3$, where the organic radicals $R^{11}$ may also be substituted by halogens and two radicals $R^{11}$ may also be joined to form a five- or six-membered ring and the radicals $R^{12}$ are each, independently of one another, hydrogen, $C_1$-$C_{22}$-alkyl, $C_2$-$C_{22}$-alkenyl, $C_6$-$C_{22}$-aryl or arylalkyl having from 1 to 10 carbon atoms in the alkyl radical and 6-20 carbon atoms in the aryl radical and two radicals $R^{12}$ may also be joined to form a five- or six-membered ring.

The three atoms $E^1$ to $E^3$ of the imine compound of the formula I or Ia and of the carbonyl compound II can be identical or different. $E^1$ to $E^3$ are each nitrogen, phosphorus or carbon, in particular nitrogen or carbon and particularly preferably carbon.

The substituents $R^1$ of the imine compound of the formula I or Ia and of the carbonyl compound of the formula II can be varied within a wide range. Possible carboorganic substituents $R^1$ are, for example, the following: $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_1$-$C_{10}$-alkyl group and/or $C_6$-$C_{10}$-aryl group as substituent, e.g. cyclopropane, cyclobutane, cyclopentane, cyclohexane, cycloheptane, cyclooctane, cyclononane or cyclododecane, $C_2$-$C_{22}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may be substituted by further alkyl groups, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, or arylalkyl which may be substituted by further alkyl groups, e.g. benzyl, o-, m-, p-methylbenzyl, 1- or 2-ethylphenyl, where, if appropriate, a radical $R^1$ may also be joined to $R^3$ to form a five-, six- or seven-membered ring which may also be a heterocycle comprising at least one atom from the group consisting of N, P, O and S. The organic radicals $R^1$ may also be substituted by halogens such as fluorine, chlorine or bromine, by amino $NR^{11}_2$, for example dimethylamino, n-pyrrolidinyl or picolinyl, by alkoxy or aryloxy $OR^{11}$, e.g. methoxy, ethoxy or isopropoxy, or organosilicon substituents $SiR^{12}_3$, e.g. trimethylsilyl, triethylsilyl, butyldimethylsilyl, tributylsilyl, tri-tert-butylsilyl, triallylsilyl, triphenylsilyl or dimethylphenylsilyl. Possible substituents $R^{11}$ are the same carboorganic radicals as described above for $R^1$, where, if appropriate, two radicals $R^{11}$ may also be joined to form a 5- or 6-membered ring and/or may be substituted by halogen. In organosilicon substituents $SiR^{12}_3$, possible radicals $R^{12}$ are the same carboorganic radicals described above for $R^1$, where, if appropriate, two radicals $R^{12}$ may also be joined to form a 5- or 6-membered ring.

Preferred radicals $R^1$ are hydrogen, methyl, ethyl, n-propyl, isopropyl, n-butyl, isobutyl, tert-butyl, n-pentyl, n-hexyl, n-heptyl, n-octyl, benzyl or phenyl, in particular methyl.

The substituents $R^3$-$R^{10}$ of the imine compound of the formula I or Ia, of the carbonyl compound of the formula II and of the aniline of the formula III can also be varied within a wide range. Possible carboorganic substituents $R^3$-$R^{10}$ are, for example, the following: $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_1$-$C_{10}$-alkyl group and/or $C_6$-$C_{10}$-aryl group as substituent, e.g. cyclopropane, cyclobutane, cyclopentane, cyclohexane, cycloheptane, cyclooctane, cyclononane or cyclododecane, $C_2$-$C_{22}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may be substituted by further alkyl groups, e.g. phenyl, naphthyl, biphenyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, or arylalkyl which may be substituted by further alkyl groups, e.g. benzyl, o-, m-, p-methylbenzyl, 1- or 2-ethylphenyl, where, if appropriate, two radicals $R^3$-$R^5$ or two radicals $R^6$-$R^{10}$ may also be joined to one another to form a five-, six- or seven-membered ring and/or a five-, six- or seven-membered heterocycle comprising at least one atom from the group consisting of N, P, O and S and/or the organic radicals $R^3$-$R^{10}$ may also be substituted by halogens such as fluorine, chlorine or bromine, amino $NR^{11}_2$, for example dimethylamino, N-pyrrolidinyl or picolinyl, alkoxy or aryloxy $OR^{11}$, e.g. methoxy, ethoxy or isopropoxy, or $SiR^{12}_3$. Furthermore, $R^3$-$R^{10}$ may be amino $NR^{11}_2$, for example dimethylamino, N-pyrrolidinyl or picolinyl, alkoxy or aryloxy $OR^{11}$, e.g. methoxy, ethoxy or isopropoxy, or halogens, such as fluorine, chlorine or bromine. Possible substituents $R^{11}$ are the same carboorganic radicals described above for $R^1$-$R^2$, where, if appropriate, two radicals $R^{11}$ may also be joined to form a 5- or 6-membered ring and/or be substituted by halogen. In organosilicon substituents $SiR^{12}_3$, possible radicals $R^{12}$ are the same carboorganic radicals described above for $R^1$-$R^2$, where, if appropriate, two radicals $R^{12}$ may also be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl.

Preferred radicals $R^3$-$R^5$ are hydrogen, methyl, trifluoromethyl, ethyl, n-propyl, isopropyl, n-butyl, isobutyl, tert-butyl, n-pentyl, n-hexyl, n-heptyl, n-octyl, benzyl, phenyl, fluorine, chlorine and bromine, in particular hydrogen.

Preferred radicals $R^6$-$R^7$ are hydrogen, methyl, trifluoromethyl, ethyl, n-propyl, isopropyl, n-butyl, isobutyl, tert-butyl, n-pentyl, n-hexyl, n-heptyl, n-octyl, benzyl, phenyl, fluorine, chlorine and bromine. $R^6$ is particularly preferably fluorine, chlorine and bromine and $R^7$ is particularly preferably a $C_1$-$C_{20}$-alkyl group, with $R^7$ preferably being bound to the aryl ring via a primary or secondary, preferably primary, carbon atom.

Preferred radicals $R^8$ and $R^{10}$ are hydrogen, methyl, ethyl, n-propyl, fluorine, chlorine and bromine, in particular hydrogen. $R^8$ and $R^{10}$ are preferably identical.

Preferred radicals $R^9$ are hydrogen, methyl, trifluoromethyl, ethyl, n-propyl, isopropyl, n-butyl, isobutyl, tert-butyl, n-pentyl, n-hexyl, n-heptyl, n-octyl, benzyl, phenyl, fluorine, chlorine and bromine, in particular hydrogen, methyl, fluorine, chlorine or bromine, very particularly preferably chlorine.

For the purposes of the present patent application, a primary carbon atom is a carbon atom having the following substitution pattern —$CH_2$-R, where R is a linear, branched or cyclic hydrocarbon radical having 1-30 carbon atoms, preferably $C_2$-$C_{22}$-alkenyl, $C_6$-$C_{22}$-aryl, arylalkyl having from 1 to 10 carbon atoms in the alkyl radical and 6-20 carbon atoms in the aryl radical or hydrogen, particularly preferably $C_1$-$C_{19}$-alkyl or hydrogen.

For the purposes of the present patent application, a secondary carbon atom is a carbon atom having the following substitution pattern —CH—$R_2$, where R is a linear, branched or cyclic hydrocarbon radical having 1-30 carbon atoms, preferably $C_1$-$C_{19}$-alkyl, $C_2$-$C_{22}$-alkenyl, $C_6$-$C_{22}$-aryl, arylalkyl having from 1 to 10 carbon atoms in the alkyl radical and 6-20 carbon atoms in the aryl radical or hydrogen, particularly preferably $C_1$-$C_{19}$-alkyl or hydrogen.

Preferred anilines of the formula III are 2-chloroaniline, 2-bromoaniline, 2,6-dichloroaniline, 2,4-dichloro-6-methylaniline or 2,6-dibromoaniline. Preference is given to $R^6$ or $R^7$ being a halogen, in particular chlorine or bromine.

The molar ratio of the carbonyl compound II to the amine G-$NH_2$ used or the aniline of the formula III is generally from 1:5 to 1:0.8, preferably from 1:2 to 1:0.9 and particularly preferably from 1:1 to 1:1.2. The order of addition of the individual components is not critical. Thus, for example, the carbonyl compound can be initially charged and the amine G-$NH_2$ or the aniline of the formula III can be added thereto.

To accelerate the reaction, it is possible to add a catalytic amount of an acid catalyst, for example $C_1$-$C_{10}$-carboxylic acids such as formic acid or acetic acid, sulfonic acids such as para-toluenesulfonic acid, also HCl, HBr, HI or $H_2SO_4$. The molar ratio of carbonyl compound II to acid catalyst is preferably in the range from 1:0.00001 to 1:0.01, preferably from 1:0.0001 to 1:0.001. Furthermore, it is possible to add reagents for absorbing the water formed in the reaction, for example molecular sieves, phosphorus pentoxide or $Si(OR)_4$, where R is a $C_1$-$C_{10}$-alkyl group.

The phosphorus pentoxide can be used as the pure substance or as a mixture with an inert solid such as aluminum oxide, silica gel or aluminosilicate. Such mixtures are commercially available under the trade name Sicapent. The molar ratio of carbonyl compound II to phosphorus pentoxide is preferably in the range from 1:0.1 to 1:100, preferably from 1:1 to 1:10 and particularly preferably from 1:1.5 to 1:3. The ratio of Sicapent (about 50% by weight water uptake capacity) to carbonyl compound II is preferably in the range from 1 g of Sicapent per 0.1 mmol of carbonyl compound II to 1 g of Sicapent per 100 mmol of carbonyl compound II, preferably from 1 g of Sicapent per 1 mmol of carbonyl compound II to 1 g of Sicapent per 10 mmol of carbonyl compound II and particularly preferably from 1 g of Sicapent per 1.8 mmol of carbonyl compound II to 1 g of Sicapent per 6 mmol of carbonyl compound II.

The order of addition of the phosphorus pentoxide is not critical; it is preferably added to the mixture of carbonyl compound II and primary amine G-$NH_2$. The total amount of phosphorus pentoxide to be used can be added at the beginning of the reaction, or it can be added at intervals in a plurality of portions during the ongoing reaction. It has been found that the process proceeds particularly quickly when the total amount of phosphorus pentoxide is added at the beginning of the reaction.

The order of addition of the acid catalyst and/or the reagent for the absorption of water is not critical; it is preferably added to the mixture of carbonyl compound II and amine G-$NH_2$.

As solvents, use is usually made of aliphatic hydrocarbons such as pentane such as n-pentane, hexane such as n-hexane and isohexane, heptane such as n-heptane, octane such as n-octane, benzene, toluene, ethylbenzene, halogenated hydrocarbons such as dichloromethane or oxygen-comprising hydrocarbons such as diethyl ether, dibutyl ether, tetrahydrofuran, ethylene glycol ethers, methanol, ethanol or isopropanol or mixtures thereof. Preference is given to using methanol, toluene or heptane when catalytic amounts of an acid catalyst are added. Preference is given to using ethers and in particular tetrahydrofuran when phosphorus pentoxide is added.

It has been found to be advantageous, particularly in the preparation of imine compounds of the formula Ia having halogen-comprising substituents on the aniline, to carry out the synthesis under a protective gas atmosphere such as nitrogen or argon.

The reaction is generally carried out at from 18 to 150° C., preferably from 30 to 110° C. and particularly preferably from 50 to 90° C. The reaction time is usually in the range from 30 minutes to 15 days, preferably from 5 hours to 5 days, particularly preferably from 8 hours to 3 days.

The work-up is carried out in a customary manner, e.g. by the filtering of the product before or after removing the solvent under reduced pressure. Purification of the product obtained can subsequently be carried out in the usual ways, for example by means of chromatography or recrystallization. An advantage of the reaction in aliphatic, nonaromatic solvents is the purity of the product obtained directly after filtration, which makes a further work-up unnecessary.

Carbonyl compounds of the formula II are prepared, for example, from 2,6-dibromopyridine as described in J. Organomet. Chem. 1973, 56, pp. 53-66.

The imine compound of the formula I can be reacted with carbonyl compounds of the formula V to form imine compounds of the formula IV.

We have accordingly found a process for preparing imine compounds of the formula IV,

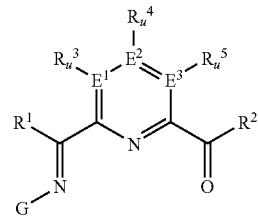

IV where the variables have the following meanings:

$R^1$-$R^2$ are each, independently of one another, hydrogen, $C_1$-$C_{22}$-alkyl, $C_2$-$C_{22}$-alkenyl, $C_6$-$C_{22}$-aryl, arylalkyl having from 1 to 10 carbon atoms in the alkyl radical and 6-20 carbon atoms in the aryl radical or a five-, six- or seven-membered heterocycle comprising at least one atom from the group consisting of N, P, O and S, where the organic radicals $R^1$-$R^2$ may also be substituted by halogens, $NR^{11}_2$, $OR^{11}$ or $SiR^{12}_3$ and/or the two radicals $R^1$-$R^2$ may also be joined to $R^3$-$R^5$ to form a five-, six- or seven-membered ring, $R^3$-$R^5$ are each, independently of one another, hydrogen, $C_1$-$C_{22}$-alkyl, $C_2$-$C_{22}$-alkenyl, $C_6$-$C_{22}$-aryl, arylalkyl having from 1 to 10 carbon atoms in the alkyl radical and 6-20 carbon atoms in the aryl radical, $NR^{11}_2$, $OR^{11}$, halogen, $SiR^{12}_3$ or a five-, six- or seven-membered heterocycle comprising at least one atom from the group consisting of N, P, O and S, where the organic radicals $R^3$-$R^5$ may also be substituted by halogens, $NR^{11}_2$, $OR^{11}$ or $SiR^{12}_3$ and/or two radicals $R^3$-$R^5$ may also be joined to one another to form a five-, six- or seven-membered ring and/or two radicals $R^3$-$R^5$ may be joined to one another to form a five-, six- or seven-membered heterocycle comprising at least one atom from the group consisting of N, P, O and S, the radicals $R^{11}$ are each, independently of one another, hydrogen, $C_1$-$C_{22}$-alkyl, $C_2$-$C_{22}$-alkenyl, $C_6$-$C_{22}$-aryl, arylalkyl having from 1 to 10 carbon atoms in the alkyl radical and 6-20 carbon atoms in the aryl radical or $SiR^{12}_3$, where the organic radicals $R^{11}$ may also be substituted by halogens and two radicals $R^{11}$ may also be joined to form a five- or six-membered ring and the radicals $R^{12}$ are each, independently of one another, hydrogen, $C_1$-$C_{22}$-alkyl, $C_2$-$C_{22}$-alkenyl, $C_6$-$C_{22}$-aryl or arylalkyl having from 1 to 10 carbon atoms in the alkyl radical and 6-20 carbon atoms in the aryl radical and two radicals $R^{12}$ may also be joined to form a five- or six-membered ring.

G is $C_1$-$C_{22}$-alkyl, $C_2$-$C_{22}$-alkenyl, $C_6$-$C_{40}$-aryl, arylalkyl having from 1 to 10 carbon atoms in the alkyl radical and 6-20 carbon atoms in the aryl radical, $NR^{11}_2$, $SiR^{12}_3$ or a five-, six- or seven-membered heterocycle comprising at least one atom from the group consisting of N, P, O and S, where the organic radical G may also be substituted by halogens, $NR^{11}_2$, $OR^{11}$ or $SiR^{12}_3$, $E^1$-$E^3$ are each, independently of one another, carbon, nitrogen or phosphorus, in particular carbon, and u is 0 when $E^1$-$E^3$ is nitrogen or phosphorus and is 1 when $E^1$-$E^3$ is carbon, which comprises the following steps:
a) reaction of an imine compound of the formula I,

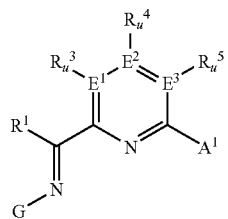

I with a metal alkyl of the formula $M^{1A}R^{1A}X^{1A}_n$, where $M^{1A}$ is Li, Na, K, Mg, Ca, Sr or Ba, in particular Li, $X^{1A}$ is $C_1$-$C_{22}$-alkyl, $C_2$-$C_{22}$-alkenyl, $C_6$-$C_{22}$-aryl, arylalkyl having from 1 to 10 carbon atoms in the alkyl radical and 6-20 carbon atoms in the aryl radical, fluorine, chlorine, bromine, iodine, hydrogen, $NR^{2A}_2$, $OR^{2A}$, $SR^{2A}$, $SO_3R^{2A}$, $OC(O)R^{2A}$, CN, SCN, where the organic radical $X^{1A}$ may also be substituted by halogens, $R^{1A}$-$R^{2A}$ are each $C_1$-$C_{22}$-alkyl, $C_2$-$C_{22}$-alkenyl, $C_6$-$C_{22}$-aryl or arylalkyl having from 1 to 10 carbon atoms in the alkyl radical and 6-20 carbon atoms in the aryl radical, where the organic radicals $R^{1A}$-$R^{2A}$ may also be substituted by halogens, and n is 0 when MIA is Li, Na or K and is 1 when MIA is Mg, Ca, Sr or Ba and b) subsequent reaction of the product obtained from step a) with a carbonyl compound of the formula V $R^{3A}$—$C(O)X^{2A}$, where $X^{2A}$ is fluorine, chlorine, bromine, iodine, $OM^{3A}$, $NR^{4A}_2$, $OR^{4A}$, $SR^{4A}$ or $OC(O)R^{4A}$, where the organic radical $X^{2A}$ may also be substituted by halogens, $R^{3A}$ is hydrogen, $C_1$-$C_{22}$-alkyl, $C_2$-$C_{22}$-alkenyl, $C_6$-$C_{22}$-aryl, arylalkyl having from 1 to 10 carbon atoms in the alkyl radical and 6-20 carbon atoms in the aryl radical or $SiR^{4A}_3$, where the organic radical $R^{3A}$ may also be substituted by halogens, and the radicals $R^{4A}$ are each, independently of one another, $C_1$-$C_{22}$-alkyl, $C_2$-$C_{22}$-alkenyl, $C_6$-$C_{22}$-aryl or arylalkyl having from 1 to 10 carbon atoms in the alkyl radical and 6-20 carbon atoms in the aryl radical and two radicals $R^{4A}$ may also be joined to form a five- or six-membered ring and $M^{2A}$ is Li, Na or K.

Preference is given to using imine compounds of the formula Ia, giving imine compounds of the formula IVa

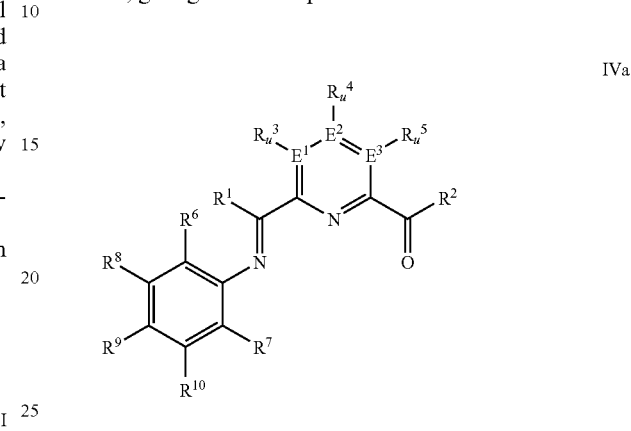

IVa where the variables have the following meanings:
$R^1$-$R^2$ are each, independently of one another, hydrogen, $C_1$-$C_{22}$-alkyl, $C_2$-$C_{22}$-alkenyl, $C_6$-$C_{22}$-aryl, arylalkyl having from 1 to 10 carbon atoms in the alkyl radical and 6-20 carbon atoms in the aryl radical or a five-, six- or seven-membered heterocycle comprising at least one atom from the group consisting of N, P, O and S, where the organic radicals $R^1$-$R^2$ may also be substituted by halogens, $NR^{11}_2$, $OR^{11}$ or $SiR^{12}_3$ and/or the two radicals $R^1$-$R^2$ may also be joined to $R^3$-$R^5$ to form a five-, six- or seven-membered ring, $R^3$-$R^{10}$ are each, independently of one another, hydrogen, $C_1$-$C_{22}$-alkyl, $C_2$-$C_{22}$-alkenyl, $C_6$-$C_{22}$-aryl, arylalkyl having from 1 to 10 carbon atoms in the alkyl radical and 6-20 carbon atoms in the aryl radical, $NR^{11}_2$, $OR^{11}$, halogen, $SiR^{12}_3$ or a five-, six- or seven-membered heterocycle comprising at least one atom from the group consisting of N, P, O and S, where the organic radicals $R^3$-$R^{10}$ may also be substituted by halogens, $NR^{11}_2$, $OR^{11}$ or $SiR^{12}_3$ and/or two radicals $R^3$-$R^5$ or two radicals $R^6$-$R^{10}$ may also be joined to one another to form a five-, six- or seven-membered ring and/or two radicals $R^3$-$R^5$ or two radicals $R^6$-$R^{10}$ may be joined to one another to form a five-, six- or seven-membered heterocycle comprising at least one atom from the group consisting of N, P, O and S, the radicals $R^{11}$ are each, independently of one another, hydrogen, $C_1$-$C_{22}$-alkyl, $C_2$-$C_{22}$-alkenyl, $C_6$-$C_{22}$-aryl, arylalkyl having from 1 to 10 carbon atoms in the alkyl radical and 6-20 carbon atoms in the aryl radical or $SiR^{12}_3$, where the organic radicals $R^{11}$ may also be substituted by halogens and two radicals $R^{11}$ may also be joined to form a five- or six-membered ring and the radicals $R^{12}$ are each, independently of one another, hydrogen, $C_1$-$C_{22}$-alkyl, $C_2$-$C_{22}$alkenyl, $C_6$-$C_{22}$-aryl or arylalkyl having from 1 to 10 carbon atoms in the alkyl radical and 6-20 carbon atoms in the aryl radical and two radicals $R^{12}$ may also be joined to form a five- or six-membered ring, $E^1$-$E^3$ are each, independently of one another, carbon, nitrogen or phosphorus, in particular carbon, and u is 0 when $E^1$-$E^3$ is nitrogen or phosphorus and is 1 when $E^1$-$E^3$ is carbon.

The definition of the variables $R^1$-$R^{12}$, G and $E^1$-$E^3$ and their preferred embodiments is the same as given further above for the imine compounds of the formulae I and Ia.

The metal alkyls $M^1R^{14}X^{14}{}_n$ are commercially available from FlukaAldrich or can be obtained, for example, by reaction of the corresponding $R^{14}$ halide with the metal $M^{14}$. Particular preference is given to lithium alkyls having a $C_1$-$C_{22}$-alkyl group, in particular a $C_1$-$C_8$-alkyl group, e.g. n-butyllithium or tert-butyllithium.

The halogen atom A of the imine compound I or Ia is usually replaced by $M^1X^{14}{}_n$ by metal-halogen exchange with the metal alkyl $M^1R^{14}X^{14}{}_n$. Particularly suitable metal alkyls are lithium alkyls, magnesium alkyls, magnesium (alkyl) halides or mixtures thereof. The molar ratio of metal alkyl to imine compound I or Ia is usually in the range from 0.4:1 to 100:1, preferably in the range from 0.9:1 to 10:1 and particularly preferably from 0.95:1 to 1.1:1. Examples of such reactions are described, inter alia, by Furukawa et al. in Tet. Lett. 28 (1987), 5845.

As solvents in reaction step a), it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The reaction can be carried out at temperatures of from −100 to +160° C., in particular from −80 to 100° C. At temperatures above 40° C., preference is given to using aromatic or aliphatic solvents which contain no ethers or have only small proportions of ethers as solvents.

The product obtained from step a) can be isolated and purified or be used directly without further work-up in step b). The product obtained from step a) is preferably used in step b) without further work-up and without isolation.

As carbonyl compounds of the formula V, preference is given to using carboxamides in which $X^{24}$ is $NR^{44}{}_2$. The carbonyl compounds V are, for example, commercially available from FlukaAldrich.

The molar ratio of carbonyl compound V to imine compound I or Ia is usually in the range from 0.4:1 to 100:1, preferably in the range from 0.9:1 to 10:1 and particularly preferably from 0.95:1 to 1.1:1. Examples of such reactions are described, inter alia, by Brandsma, Preparative Polar Organic Chemistry, pp. 30-31 and pp. 142-143, Springer Verlag 1987.

As solvents in reaction step b), it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The reaction can be carried out at temperatures of from −100 to +160° C., in particular from −80 to 100° C. At temperatures above 40° C., preference is given to using aromatic or aliphatic solvents which contain no ethers or have only small proportions of ethers as solvents.

The process of the invention is particularly useful for anilines of the formula III having at least one halogen atom in the ortho position. Such anilines give only low yields of imine compound IV in toluene or alcohol.

The imine compounds of the formula IV or IVa obtained in this way can be reacted with further amine G-$NH_2$ or with further aniline of the formula III to give bis(imino) compounds. This synthetic route is particularly useful for preparing unsymmetrical bis(imino) compounds.

For the present purposes, unsymmetrical bis(imino) compounds are compounds which comprise at least two imino groups whose aryl radicals are not identically substituted. This is based on the substituents or the substitution pattern of the substituents under the theoretical assumption that the aryl radicals can rotate freely.

The preparation of the unsymmetrical bis(imino) compounds from imine compounds of the formula IV or IVa and further amine G-$NH_2$ or aniline of the formula III can be carried out under the same conditions as have been described for the process of the invention for preparing the imine compounds of the formula I or Ia.

Particularly preferred unsymmetrical bisimine compounds made from imine compounds of the formula IV are 2-[1-(2,6-dimethylphenylimino)ethyl]-6-[1-(2,4-dichloro-6-methylphenylimino)ethyl]pyridine, 2-[1-(2,4,6-trimethylphenylimino)ethyl]-6-[1-(2,4-dichloro-6-methylphenylimino)ethyl]pyridine, 2-[1-(2,6-dimethylphenylimino)ethyl]-6-[1-(2-chloro-6-methylphenylimino)ethyl]pyridine, 2-[1-(2,4,6-trimethylphenylimino)ethyl]-6-[1-(2-chloro-6-methylphenylimino)ethyl]pyridine, 2-[1-(2,6-diisopropylphenylimino)ethyl]-6-[1-(2-chloro-6-methylphenylimino)ethyl]pyridine, 2-[1-(2,6-dimethylphenylimino)ethyl]-6-[1-(2,4-dibromo-6-methylphenylimino)ethyl]pyridine, 2-[1-(2,6-dimethylphenylimino)ethyl]-6-[1-(2-bromo-6-methylphenylimino)ethyl]pyridine, 2-[1-(2,4,6-trimethylphenyl-imino)ethyl]-6-[1-(2-bromo-6-methylphenylimino)ethyl]pyridine and 2-[1-(2,6-diisopropylphenylimino)ethyl]-6-[1-(2-bromo-6-methylphenylimino)ethyl]pyridine.

The unsymmetrical bis(imino) compounds can be reacted further to form the corresponding titanium, zirconium, vanadium, chromium, iron or cobalt complexes. These are suitable as catalysts for the polymerization of olefins.

The process of the invention enables, in particular, even anilines having electron-pulling substituents to be converted into the corresponding monoimine compounds in good yields.

The imine compounds IVa are thermodynamically very stable and can be reacted with further aniline to form the unsymmetrical bisimine compounds. If imine compounds which are not substituted by electron-pulling radicals in the ortho position are used as starting materials, a further reaction with further aniline usually leads to mixtures of various symmetrical and unsymmetrical bisimine compounds.

A further advantage is that the process is also very well suited to the preparation of commercial quantities. Furthermore, 2,6-dibromopyridine is a cheaper starting material than, for example, 2,6-diacetylpyridine.

The following experimental examples serve to illustrate the invention without restricting the scope of the invention.

EXAMPLES

Example 1

Preparation of 1-(6-bromopyridin-2-yl)ethylidene](2-chloro-4,6-dimethylphenyl)amine

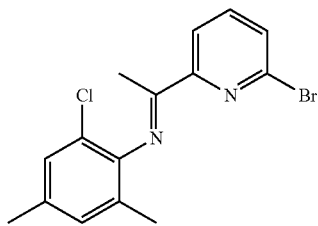

1.00 g (0.0050 mol) of 1-acetyl-6-bromopyridine, 1.32 g (0.0085 mol) of 2,4-dimethyl-6-chloroaniline and 1 g of Sicapent were heated under reflux in 25 ml of tetrahydrofuran for 7.5 hours. After cooling, the insoluble solid was filtered off and washed with tetrahydrofuran. The solvent was distilled off from the filtrate obtained in this way and the residue was purified by column chromatography (aluminum oxide, neutral) (heptane:ethyl acetate=4:1), $r_f$=0.1. This gave 0.80 g (0.0024 mol) of the product in a yield of 48%.

Example 2

Preparation of 1-{6-[1-(2-chloro-4,6-dimethylphenylimino)ethyl]pyridin-2-yl}ethanone

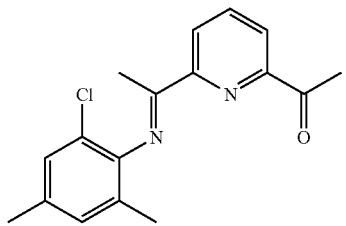

2.00 g (0.0059 mol) of [1-(6-bromopyridin-2-yl)ethylidene](2-chloro-4,6-dimethylphenyl)amine were dissolved in 25 ml of diethyl ether and cooled to −70° C. 3.70 ml (0.0059 mol) of a 1.6 M solution of butyllithium in hexane were added dropwise over a period of 15 minutes. The temperature rose to −40° C. and the mixture was stirred for another 30 minutes. The mixture was cooled to −70° C. and 0.52 g (0.0059 mol) of N,N-dimethylacetamide was added dropwise and the mixture was stirred at room temperature for another three hours. The reaction mixture was stirred with 5 ml of a saturated ammonium chloride solution. The aqueous phase was extracted twice with diethyl ether. The combined organic phases were dried over $Na_2SO_4$, filtered and the solvent was distilled off under reduced pressure. This gave 0.83 g (0.0028 mol) of the product in a yield of 47%.

Comparative Example 1

Preparation of 1-{6-[1-(2-chloro-4,6-dimethylphenylimino)ethyl]pyridin-2-yl}ethanone in methanol 10 g of 2,6-diacetylpyridine (0.0613 mol), 9.54 g of 2-chloro-4,6-dimethylaniline (0.0613 mol) and 0.6 g of p-toluenesulfonic acid were heated under reflux in 400 ml of methanol for 90 minutes using a water separator. The solvent was distilled off completely and the residue was recrystallized twice from 50 ml of isopropanol. This gave 0.92 g (0.0031 mol) of 1-{6-[1-(2-chloro-4,6-dimethylphenylimino)ethyl]pyridin-2-yl}ethanone in a yield of 5%.

The GC/MS indicated a product purity of 72%.

The invention claimed is:

1. A process for making a 6-acetyl-(2-arylimino)pyridine, useful as an intermediate for making unsymmetric bis(arylimino)pyridines, said process comprising:
   (a) reacting a 6-halo-2-acetylpyridine with an aniline in the presence of an acid catalyst and a dehydrating agent to give a 6-halo-2-(arylimino)pyridine; and
   (b) converting the 6-halo-2-(arylimino)pyridine to a 6-acetyl-(2-arylimino)pyridine by metallation, acetyl transfer, and acidic workup.

2. The process of claim 1 wherein the aniline has at least one halogen atom in the ortho position.

3. The process of claim 2 wherein the aniline is selected from the group consisting of 2-chloroaniline, 2-bromoaniline, 2,6-dichloroaniline, 2,4-dichloro-6-methylaniline, and 2,6-dibromoaniline.

4. The process of claim 1 wherein the resulting 6-acetyl-(2-arylimino) pyridine is converted to an unsymmetric bis(arylimino)pyridine.

5. A process for preparing imine compounds of the formula:

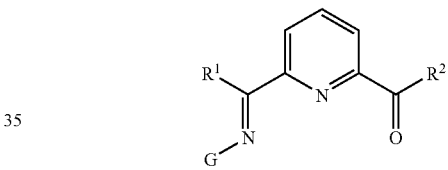

wherein $R^1$ and $R^2$ are each independently hydrogen or $C_1$-$C_{22}$-alkyl and G is $C_6$-$C_{40}$-aryl or arylalkyl having from 1 to 10 carbon atoms in the alkyl radical and 6-20 carbon atoms in the aryl radical, where G may also be substituted by halogens;

said process comprising:
(a) reacting an imine compound of the formula

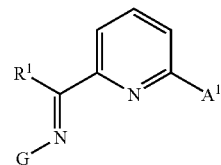

wherein $A^1$ is chlorine, bromine or iodine; and $R^1$ and G are as defined above; with a metal alkyl of the formula $M^{1A}R^{1A}$, wherein $M^{1A}$ is Li, Na, or K; and $R^{1A}$ is $C_1$-$C_{22}$-alkyl; and
(b) reacting the product from step (a) with a carbonyl compound of the formula $R^{3A}$-C(O)$NR^{4A}_2$, where $R^{3A}$ is hydrogen or $C_1$-$C_{22}$-alkyl; and $R^{4A}$ is $C_1$-$C_{22}$-alkyl.

6. The process of claim 4 wherein $M^{1A}$ is Li.

7. The process of claim 4 wherein G has at least one halogen atom in the ortho position.

* * * * *